US006811975B2

(12) United States Patent
Cook et al.

(10) Patent No.: US 6,811,975 B2
(45) Date of Patent: Nov. 2, 2004

(54) PHOSPHOROTHIOATE OLIGONUCLEOTIDES HAVING MODIFIED INTERNUCLEOSIDE LINKAGES

(75) Inventors: Phillip Dan Cook, Lake San Marcos, CA (US); Muthiah Manoharan, Carlsbad, CA (US)

(73) Assignee: ISIS Pharmaceuticals, Inc., Carlsbad, CA (US)

( * ) Notice: Subject to any disclaimer, the term of this patent is extended or adjusted under 35 U.S.C. 154(b) by 262 days.

(21) Appl. No.: 09/805,630

(22) Filed: Mar. 14, 2001

(65) Prior Publication Data

US 2001/0027251 A1 Oct. 4, 2001

Related U.S. Application Data

(62) Division of application No. 09/115,027, filed on Jul. 14, 1998, now Pat. No. 6,242,589.

(51) Int. Cl.[7] .......................... C12Q 1/68; C07H 21/04

(52) U.S. Cl. ..................... 435/6; 536/24.3; 536/24.31; 536/24.32; 536/24.33

(58) Field of Search ............................ 536/24.5, 24.3, 536/24.31, 24.32, 24.33, 25.3, 25.31, 26.31; 435/7, 6

(56) References Cited

U.S. PATENT DOCUMENTS

| | | | |
|---|---|---|---|
| 3,687,808 A | | 8/1972 | Merigan et al. |
| 4,689,320 A | | 8/1987 | Kaji |
| 4,806,463 A | | 2/1989 | Goodchild et al. |
| 5,004,810 A | | 4/1991 | Draper |
| 5,166,195 A | | 11/1992 | Ecker |
| 5,194,428 A | | 3/1993 | Agrawal et al. |
| 5,212,295 A | | 5/1993 | Cook |
| 5,242,906 A | | 9/1993 | Pagano et al. |
| 5,248,670 A | | 9/1993 | Draper et al. |
| 5,442,049 A | | 8/1995 | Anderson et al. |
| 5,457,189 A | | 10/1995 | Crooke et al. |
| 5,489,677 A | | 2/1996 | Sanghvi et al. |
| 5,500,357 A | * | 3/1996 | Taira et al. ............... 435/91.31 |
| 5,514,577 A | | 5/1996 | Draper et al. |
| 5,514,788 A | | 5/1996 | Bennett et al. |
| 5,523,389 A | | 6/1996 | Ecker et al. |
| 5,580,767 A | | 12/1996 | Cowsert et al. |
| 5,582,972 A | | 12/1996 | Lima et al. |
| 5,582,986 A | | 12/1996 | Monia et al. |
| 5,587,361 A | | 12/1996 | Cook et al. |
| 5,591,600 A | | 1/1997 | Ecker |
| 5,591,623 A | | 1/1997 | Bennett et al. |
| 5,591,720 A | | 1/1997 | Anderson et al. |
| 5,599,797 A | | 2/1997 | Cook et al. |
| 5,607,923 A | | 3/1997 | Cook et al. |
| 5,620,963 A | | 4/1997 | Cook et al. |
| 5,658,891 A | | 8/1997 | Draper et al. |
| 5,661,134 A | | 8/1997 | Cook et al. |
| 5,681,747 A | | 10/1997 | Boggs et al. |
| 5,681,944 A | | 10/1997 | Crooke et al. |
| 5,691,461 A | | 11/1997 | Ecker et al. |
| 5,824,519 A | * | 10/1998 | Norris et al. ............ 435/91.31 |
| 5,912,149 A | * | 6/1999 | Ruiz et al. ............... 435/320.1 |
| 6,060,456 A | | 5/2000 | Arnold, Jr. et al. |
| 6,242,589 B1 | * | 6/2001 | Cook et al. ................ 536/24.5 |

FOREIGN PATENT DOCUMENTS

| WO | WO 94/08003 | | 4/1994 |
|---|---|---|---|
| WO | WO 98/24925 | * | 6/1998 |

OTHER PUBLICATIONS

Ohta et al. Tissue–specific expression of an anti–ras ribozyme inhibits proliferation of human malignant melanoma cells. Nucleic acid Research, vol. 24. No. 5, pp. 938–942.*

Stanley–Crooke, Antisense Research and Applications, Chapter 1, Basic Principles of Antisense Therapeutics, Springer–Verlag Press, Berlin, Heidelberg, New York, p. 3.*

Andrea D. Branch, A good antisense molecule is hard to find, TIBS, 47–48.*

The above references were forwarded to Applicants during the prosecution of parent case 09/338,942.*

Albert, P.R. et al., "Antisense knockouts: molecular scalpels for the dissection of signal transduction", *Trends Pharmacol. Sci.,* 1994, 15, 250–254.

Berkow et al. (eds.), *The Merck Manual of Diagnosis and Therapy,* Rahway, N.J., 1987, 15th Edition, 2263–2277, 2283–2292, 2301–2310.

Bernhard et al., "Direct Evidence Linking Expression of Matrix Metalloproteinase 9 (92–kDa gelatinase/collagenase) to the metastatic phenotype in transformed rat embryo cells," *Proc. Natl. Acad. Sci. USA,* 1994, 91, 4293–4297.

Birkedal–Hansen, "Proteolytic Remodeling of Extracellular Matrix," *Curr. Op. Cell Biol.,* 1995, 7, 728–735.

Boggemeyer et al., "*Borrelia Burgdorferi* Upregulates the Adhesion Molecules E–selectin, P–selectin, ICAM–1 and VCAM–1 on Mouse Endothelioma Cells in vitro," *Cell Adhes. Commun.,* 1994, 2, 145–157.

Cook, P.D., "Medicinal chemistry of antisense oligonucleotides—future opportunities", *Anti–Cancer Drug Design,* 1991, 6, 585–607.

Crooke, S.T. et al., "Pharmacokinetic Properties of Several Novel Oligonucleotide Analogs in mice", *J. Pharmacol. Exp. Therapeutics,* 1996, 277, 923–937.

Crooke, S.T., "Progress in Antisense Therapeutics", *Ann. Rev. Pharmacol. Toxicol.,* 1996, 36, 107–129.

(List continued on next page.)

Primary Examiner—Janet L. Epps-Ford
(74) *Attorney, Agent, or Firm*—Isis Patent Department; Woodcock Washburn LLP

(57) ABSTRACT

Novel compounds that mimic and/or modulate the activity of wild-type nucleic acids. In general, the compounds are phosphorothioate oligonucleotides wherein the 5'-terminal internucleoside linkage or the 5'- and 3'-terminal linkages are modified.

15 Claims, 2 Drawing Sheets-

OTHER PUBLICATIONS

Dean, N.M. et al., "Inhibition of protein kinase C–α expression in mice after systemic administration of phosphorthioate antisense oligodeoxynucleotides", *Proc. Natl. Acad. Sci.*, 1994, 91, 11762–11766.

DeLisser et al., "Molecular and Functional Aspects of PECAM–1/CD31," *Immunol. Today*, 1994, 15(10), 490–494.

Dimock et al., "An efficient multigram synthesis of monomers for the preparation of novel oligonucleotides containing isosteric non–phosphorous backbones", *Nucleosides & Nucleotides*, 1997, 16(7–9), 1629–1632.

Downward, "The ras Superfamily of Small GTP–binding proteins," *TIBS, 15*, 1990, 469–472.

Englisch, U. et al., "Chemically Modified Oligonucleotides as Probes and Inhibitors", *Angew. Chem. Int. Ed. Eng.*, 1991, 30, 613–629.

Griffiths, C.E.M. et al., "Keratinocyte Intercellular Adhesion Molecule–1 (ICAM–1) Expression Preceeds Derman T Lymphocyte Infiltration in Allergic Contact Dermatitis (*Rhus dermatitis*)", *Am. J. Pathology.*, 1989, 135, 1045–1053.

Gum et al., "Stimulation of 92–kDa Gelatinase B Promoter Activity by ras Is Mitogen–activated Protein Kinase Kinase 1–independent and Requires Multiple Transcription Factor Binding Sites Including Closely Spaced PEA3/ets and AP–1 Sequences," *J. Biol. Chem.*, 1996, 271(18), 10672–10680.

Guzaev et al., "Synthesis of $^{14}$C–Radiolabeled Oligonucleotides with a Novel Phosphoramidite Reagent", *Bioorg. Med. Chem. Lett.*, 1998, 8, 1123–1126.

Hakugawa et al., "The Inhibitory Effect of Anti–Adhesion Molecule Antibodies on Eosinophil Infilration in Cutaneous Late Phase Response in Balb/c Mice Sensitized with Ovalbumin (OVA)," *J. Dermatol.*, 1997, 24, 73–79.

Hegemann, L. et al., "Biochemical Pharmacology of Protein Kinase C and its Relevance for Dermatology", *Pharmacology of the Skin*, Mukhtar, H. (ed.), CRC Press, Boca Raton, 1992, Ch. 22, 357–268.

Himelstein et al., "Metalloproteinases in Tumor Progression: The Contribution of MMP–9," *Invasion & Metastasis*, 1995–95, 14, 246–258.

Ho, V.C. et al., "Treatment of severe lichen planus with cyclosporine", *J. Am. Acad. Dermatol.*,1990, 22, 64–68.

Hua et al., "Inhibition of Matarix Metalloproteinase 9 Expression by a Ribozyme Blocks Metastasis in a Rat Sarcoma Model System," *Cancer Res.*, 1996, 56, 5279–5284.

Hurtenbach et al., "Prednisolone Reduces Experimental Arthritis and Inflammatory Tissue Destruction in Scid Mice Infected with *Borrelia Burgorferi,*" *Int. J. Immunopharmac,* 1996, 18(5), 281–288.

Iyer, R.P. et al., "The Automated Synthesis of Sulfur–Containing Oligodeoxyribonucleotides Using 3H–1, 1–Benzodithiol–3–one 1,4–Dioxide as a Sulfur–Transfer Reagent", *J. Org. Chem.*, 1990, 55, 4693–4699.

Kabanov, A.V., "A new class of antivirals: antisense olgonucleotides combined with a hydrophobic substituent effectively inhibit influenza virus reproduction and synthesis of virus–specific proteins in MDCK cells", *FEBS Letts.*, 1990, 259, 327–330.

Katocs, A.S. et al., "Biological Testing", *Remington's Pharmaceutical Sciences*, 18th Ed., Gennaro (ed.), Mack Publishing Co., Easton, PA, 1990, Ch. 27, 484–494.

Kerr et al., "Growth Factors Regulate Transin Gene Expression by c–fos–Dependent and c–fos–Independent Pathways," *Science*, 1988, 242, 1424–1427.

Kerr et al., "TGFβ1 Inhibition of Transin/Stromelysin Gene Expression Is Mediated Through a Fos Binding Sequence," *Cell*, 1990, 61, 267–278.

Kroschwitz, J.I., "Polynucleotides", *Concise Encyclopedia of Polymer Science and Engineering*, 1990, John Wiley & Sons, New York; 858–859.

Letsinger, R.L. et al., "Cholesteryl–conjugated oligonucleotides: Synthesis, properties and activity as inhibitors of replication of human immunodeficiency virus in cell culture", *Proc. Natl. Acad. Sci.*, 1989, 86, 6553–6556.

Lisby, S. et al., "Intercellular adhesion molecule–1 (ICAM–1) expression correlated to inflammation", *Br. J. Dermatol.*, 1989, 120, 479–484.

Litwin et al., "Novel Cytokine–independent Induction of Endothelial Adhesion Molecules Regulate by Platelet/Endothelial Cell Adhesion Molecule (CD31)," *J. Cell Biol.*, 1997, 139(1), 219–228.

Manoharan, M. et al., "Lipidic Nucleic Acids", *Tetrahedron Letts.*, 1995, 36, 3651–3654.

Manoharan M. et al., "Cholic Acid–0ligonucliotide Conjugates for Antisense Applications", *Bioorganic Med. Chem. Letts.*, 1994, 4, 1053–1060.

Manoharan, M. et al., "Introduction of a Lipophilic Thioether Tether in the Minor Groove of Nucleic Acids for Antisense Applications", *Bioorg. Med. Chem. Letts.*, 1993, 3, 2765–2770.

Manoharan, M. et al., "Chemical Modifications to Improve Uptake and Bioavailability of Antisense Oligonucleotides", *Annals NY Acad. Sciences*, 1992, 660, 306–309.

Manoharan M. et al., "Oligonucleotide Conjugates: Alteration of the Pharmacokinetic Properties of Antisense Agents", *Nucleosides and Nucleotides*, 1995, 14, 969–973.

Martin, P., "Ein neuer Zugang zu 2'–O–Alkylribonucleosiden und Eigenschaften deren Oligonucleotide", *Helvetica Chemica Acta*, 1995, 78, 486–504.

Mishra, R.K. et al., "Improved leishmanicidal effect of phosphorotioate antisense oligonucleotides by LDL–medicated delivery,", *Biochim. Et Biophysica*, 1995, 1264, 229–237.

Newman, "Perspective Series: Cell Adhesion in Vascular Biology," *The Biology of PECAM–1, J. Clin. Invest.*, 1997, 99(1), 3–7.

Nies, A.S. et al., "Principles of Therapeutics", *Goodman & Gilman's The Pharmacological Basis of Therapeutics*, 9th Ed., Hardman et al. (eds.), McGraw–Hill, New York, NY, 1996, ch. 3, 43–62.

Oberhauser, B. et al., "Effective incorporation of 2'–O–methyl–oligonucleotides into liposomes and enhanced cell association through modification with thiocholesterol" *Nucl. Acids Res.*, 1992, 20, 533–538.

Regezi et al., "Vascular adhesion molecules in oral lichen planus," *Oral Surg. Oral Med. Oral Pathol.*, 1996, 81, 682–690.

Ruoslahti, "How Cancer Spreads," *Sci. Am.*, 1996, 72–77.

Saison–Behmoaras, T. et al., "Short modified antisense oligonucleotides directed against Ha–ras point mutation induce selective cleavage of the mRNA and inhbit T24 cells proliferation", *EMBO J.*, 1991, 10, 1111–1118.

Sanghvi et al., "Concept, Discovery and Development of MMI Linkage: Story of a Novel Linkage for Antisense Constructs", *Nucleosides & Nucleotides,* 1997, 16(7–9), 907–916.

Sanghvi, Y.S., "Heterocyclic Base Modifications in Nucleic acids and their Applications in Antisense Oligonucleotides", *Antisense Research and Applications,* Crooke et al. (Eds.), CRC Press, Boca Raton, 1993, Chapter 15, 273–288.

Secrist, J.A. et al., "Synthesis and Biological Activity of 4'-Thionucleosides", *10th International Rountable: Nucleosides, Nucleotides and their Biological Applications,* Sep. 16–20, 1992, Abstact 21, Park City, Utah, 40.

Shea, R.G. et al., "Synthesis, hybridization properties and antiviral activity of lipid–oligodeoxynucletide conjugates", *Nucl. Acids Res.,* 1990, 18, 3777–3783.

Shiohara et al., "Fixed drug Eruption: Expression of Epidermal Keratinocyte Intercellular Adhesion Molecule–1 (ICAM–1)", *Arch. Dermatol.,* 1989 125, 1371–1376.

Stetler–Stevenson et al., "Tumor Cell Interactions with the Extracellular Matrix During Invasion and Metastasis," *Annu. Rev. Cell Biol.,* Palade, G.E. et al. (eds.), 1993, 9, 541–573.

Svinarchuk, F.P. et al., "Inhibition of HIV proliferation in MT–4 cells by antisense oligonucleotide conjugated to lipophilic groups", *Biochimie,* 1993, 79, 49–54.

Swayze et al., "The Synthesis of N,N'–O–Trisubstituted Hydroxylamines via a Mild Reductive Alkylation Procedure: An Improved Synthesis of the MMI Backbone", *Synlett,* 1997, 859–861.

Swayze et al., "The Synthesis of the Sixteen Possible 2'–O–Methyl MMI Dimer Phosphoramidites: Building Blocks for the Synthesis of Novel Antisense Oligonucleotides", *Nucleosides & Nucleotides,* 1997, 16(7–9), 971–972.

U.S. Congress, Office of Technology Assessment, "The State–of–the–art in Genetic Screening", *Genetic Monitoring and Screening in the Workplace,* OTA–BA–455, U.S. Government Printing Office, Washington, D.C., 1990, Ch. 5, 75–99.

Wahlestedt, C. et al., "Antisense oligodeoxynucleotides to NMDA–R1 receptor channel protect cortical neurons from excitotoxicity and reduce focal ischaemic infarctions", *Nature,* 1993, 363, 260–263.

Wahlestedt, C. et al., "Modulation of Anxiety and Neuropeptide Y–Y1 Recptors by Antisense Oligodeoxynucleotides", *Science,* 1993, 259, 528–531.

Ausubel, F.M. et al. (Eds.), *Current Protocols in Molecular Biology,* Current Publications, 1993.

Sambrook, J. et al. (Eds.), *Molecular Cloning, A Laboratory Manual,* Second Ed., Cold Spring Harbor Laboratory Press, 1989.

* cited by examiner

SEQUENCE LISTING

```
<160> NUMBER OF SEQ ID NOS: 17

<210> SEQ ID NO 1
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (19)..(20)
<223> OTHER INFORMATION: MMI linkage

<400> SEQUENCE: 1
tgcatccccc aggccaccat                                              20

<210> SEQ ID NO 2
<211> LENGTH: 18
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(2)
<223> OTHER INFORMATION: MMI linkage

<400> SEQUENCE: 2
tgcatccccc aggccacc                                                18

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 3
tgcatccccc aggcgaccat                                              20

<210> SEQ ID NO 4
<211> LENGTH: 20
<212> TYPE: DNA
<213> ORGANISM: Artificial Sequence
```

```
<220> FEATURE:
<223> OTHER INFORMATION: Oligonucleotide primer

<400> SEQUENCE: 4
tgcatccccc aggccaccat                                               20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(2)
<223> OTHER INFORMATION: MMI linkage
<220> FEATURE:
<221> NAME/KEY: misc_feature
<222> LOCATION: (19)..(20)
<223> OTHER INFORMATION: MMI linkage

<400> SEQUENCE: 5
tgcatccccc aggccaccat                                               20

<210> SEQ ID NO 6
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 6
tccgtcatcg ctcctcaggg                                               20

<210> SEQ ID NO 7
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 7
ttagtaatag ccccacatgg                                               20

<210> SEQ ID NO 8
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(2)
<223> OTHER INFORMATION: MMI (1+1), phosphorothioate
<220> FEATURE:
<221> NAME/KEY: misc_feature
<222> LOCATION: (19)..(20)
<223> OTHER INFORMATION: MMI (2+2), phosphorothioate

<400> SEQUENCE: 8
tccgtcatcg ctcctcaggg                                               20

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide primer
<220> FEATURE:
```

```
<221> NAME/KEY: misc_feature
<222> LOCATION: (1)..(4)
<223> OTHER INFORMATION: MMI (2+2), phosphorothioate
<220> FEATURE:
<221> NAME/KEY: misc_feature
<222> LOCATION: (17)..(20)
<223> OTHER INFORMATION: MMI (2+2), phosphorothioate

<400> SEQUENCE: 9
tccgtcatcg ctcctcaggg                                                   20

<210> SEQ ID NO 10
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(6)
<223> OTHER INFORMATION: MMI (3+3), phosphorothioate
<220> FEATURE:
<221> NAME/KEY: misc_feature
<222> LOCATION: (15)..(20)
<223> OTHER INFORMATION: MMI (3+3), phosphorothioate

<400> SEQUENCE: 10
tccgtcatcg ctcctcaggg                                                   20

<210> SEQ ID NO 11
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(4)
<223> OTHER INFORMATION: MMI (2+2), phosphodiester
<220> FEATURE:
<221> NAME/KEY: misc_feature
<222> LOCATION: (17)..(20)
<223> OTHER INFORMATION: MMI (2+2), phosphodiester

<400> SEQUENCE: 11
tccgtcatcg ctcctcaggg                                                   20

<210> SEQ ID NO 12
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(6)
<223> OTHER INFORMATION: MMI (3+3), phosphodiester
<220> FEATURE:
<221> NAME/KEY: misc_feature
<222> LOCATION: (15)..(20)
<223> OTHER INFORMATION: MMI (3+3), phosphodiester

<400> SEQUENCE: 12
tccgtcatcg ctcctcaggg                                                   20

<210> SEQ ID NO 13
<211> LENGTH: 20
<212> TYPE: DNA
<213> ORGANISM: Artificial Sequence
<220> FEATURE:
<223> OTHER INFORMATION: Oligonucleotide primer
```

```
<400> SEQUENCE: 13
tccgtcatcg ctcctcaggg                                           20

<210> SEQ ID NO 14
<211> LENGTH: 20
<212> TYPE: DNA
<213> ORGANISM: Artificial Sequence
<220> FEATURE:
<223> OTHER INFORMATION: Oligonucleotide primer

<400> SEQUENCE: 14
ttagtaatag ccccacatgg                                           20

<210> SEQ ID NO 15
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(3)
<223> OTHER INFORMATION: methoxy ethyl, phosphorothioate
<220> FEATURE:
<221> NAME/KEY: misc_feature
<222> LOCATION: (13)..(20)
<223> OTHER INFORMATION: methoxy ethyl, phosphorothioate

<400> SEQUENCE: 15
tccgtcatcg ctcctcaggg                                           20

<210> SEQ ID NO 16
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(2)
<223> OTHER INFORMATION: MMI (1+1), phosphorothioate
<220> FEATURE:
<221> NAME/KEY: misc_feature
<222> LOCATION: (19)..(20)
<223> OTHER INFORMATION: MMI (1+1), phosphorothioate

<400> SEQUENCE: 16
tccgtcatcg ctcctcaggg                                           20

<210> SEQ ID NO 17
<211> LENGTH: 20
<212> TYPE: DNA
<213> ORGANISM: Artificial Sequence
<220> FEATURE:
<223> OTHER INFORMATION: Oligonucleotide primer
<220> FEATURE:
<221> NAME/KEY: misc_feature
<222> LOCATION: (1)..(4)
<223> OTHER INFORMATION: MMI (2+2), phosphorothioate
<220> FEATURE:
<221> NAME/KEY: misc_feature
<222> LOCATION: (17)..(20)
<223> OTHER INFORMATION: MMI (2+2), phosphorothioate

<400> SEQUENCE: 17
tccgtcatcg ctcctcaggg                                           20
```

PHOSPHOROTHIOATE OLIGONUCLEOTIDES HAVING MODIFIED INTERNUCLEOSIDE LINKAGES

RELATED APPLICATIONS

This application is a divisional of U.S. patent application Ser. No. 09/115,027, filed Jul. 14, 1998, now U.S. Pat. No. 6,242,589, which is incorporated herein in its entirety.

FIELD OF THE INVENTION

This invention relates to the design and synthesis of nuclease resistant phosphorothioate oligonucleotides which are useful for therapeutics, diagnostics and as research reagents. Phosphorothioate oligonucleotides are provided in which at least one terminal, internucleoside linkage is modified. Such compounds are resistant to nuclease degradation and are capable of modulating the activity of DNA and RNA.

BACKGROUND OF THE INVENTION

It is well known that most of the bodily states in multicellular organisms, including most disease states, are effected by proteins. Such proteins, either acting directly or through their enzymatic or other functions, contribute in major proportion to many diseases and regulatory functions in animals and man. For disease states, classical therapeutics has generally focused upon interactions with such proteins in efforts to moderate their disease-causing or disease-potentiating functions. In newer therapeutic approaches, modulation of the actual production of such proteins is desired. By interfering with the production of proteins, the maximum therapeutic effect can be obtained with minimal side effects. It is therefore a general object of such therapeutic approaches to interfere with or otherwise modulate gene expression, which would lead to undesired protein formation.

One method for inhibiting specific gene expression is with the use of oligonucleotides, especially oligonucleotides which are complementary to a specific target messenger RNA (mRNA) sequence. Several oligonucleotides are currently undergoing clinical trials for such use. Phosphorothioate oligonucleotides are presently being used as therapeutic agents in human clinical trials against various disease states, including use as antiviral agents.

In addition to such use as both indirect and direct regulators of proteins, oligonucleotides also have found use in diagnostic tests. Such diagnostic tests can be performed using biological fluids, tissues, intact cells or isolated cellular components. As with gene expression inhibition, diagnostic applications utilize the ability of oligonucleotides to hybridize with a complementary strand of nucleic acid. Hybridization is the sequence specific hydrogen bonding of oligomeric compounds via Watson-Crick and/or Hoogsteen base pairs to RNA or DNA. The bases of such base pairs are said to be complementary to one another.

Oligonucleotides are also widely used as research reagents. They are useful for understanding the function of many other biological molecules as well as in the preparation of other biological molecules. For example, the use of oligonucleotides as primers in PCR reactions has given rise to an expanding commercial industry. PCR has become a mainstay of commercial and research laboratories, and applications of PCR have multiplied. For example, PCR technology now finds use in the fields of forensics, paleontology, evolutionary studies and genetic counseling. Commercialization has led to the development of kits which assist non-molecular biology-trained personnel in applying PCR. Oligonucleotides, both natural and synthetic, are employed as primers in such PCR technology.

Oligonucleotides are also used in other laboratory procedures. Several of these uses are described in common laboratory manuals such as *Molecular Cloning, A Laboratory Manual*, Second Ed., J. Sambrook, et al., Eds., Cold Spring Harbor Laboratory Press, 1989; and *Current Protocols In Molecular Biology*, F. M. Ausubel, et al., Eds., Current Publications, 1993. Such uses include as synthetic oligonucleotide probes, in screening expression libraries with antibodies and oligomeric compounds, DNA sequencing, in vitro amplification of DNA by the polymerase chain reaction, and in site-directed mutagenesis of cloned DNA. See Book 2 of *Molecular Cloning, A Laboratory Manual*, supra. See also "DNA-protein interactions and The Polymerase Chain Reaction" in Vol. 2 of *Current Protocols In Molecular Biology*, supra.

A number of chemical modifications have been introduced into oligonucleotides to increase their usefulness in diagnostics, as research reagents and as therapeutic entities. Such modifications include those designed to increase binding to a target strand (i.e. increase melting temperatures, Tm), to assist in identification of an oligonucleotide or an oligonucleotide-target complex, to increase cell penetration, to stabilize against nucleases and other enzymes that degrade or interfere with the structure or activity of the oligonucleotides, to provide a mode of disruption (terminating event) once sequence-specifically bound to a target, and to improve the pharmacokinetic properties of the oligonucleotide.

The complementarity of oligonucleotides has been used for inhibition of a number of cellular targets.

Complementary oligonucleotides are commonly described as being antisense oligonucleotides. Various reviews describing the results of these studies have been published including Progress In Antisense Oligonucleotide Therapeutics, Crooke, S. T. and Bennett, C. F., *Annu. Rev. Pharmacol. Toxicol.*, 1996, 36, 107–129. These oligonucleotides have proven to be powerful research tools and diagnostic agents. Certain oligonucleotides that have been shown to be efficacious are currently in human clinical trials.

The pharmacological activity of oligonucleotides, like other therapeutics, depends on a number of factors that influence the effective concentration of these agents at specific intracellular targets. One important factor for oligonucleotides is the stability of the species in the presence of nucleases. It is unlikely that unmodified, naturally-occurring oligonucleotides will be useful therapeutic agents because they are rapidly degraded by nucleases. The limitations of available methods for modification of the phosphate backbone of unmodified oligonucleotides have led to a continuing and long felt need for other modifications which provide resistance to nucleases and satisfactory hybridization properties for antisense oligonucleotide diagnostics and therapeutics.

SUMMARY OF THE INVENTION

The present invention provides compounds that mimic and/or modulate the activity of wild-type nucleic acids. In general, the compounds contain a selected sequence of covalently bound nucleosides which is specifically hybridizable with a targeted nucleoside sequence of single stranded or double stranded DNA or RNA.

In preferred embodiments, the compounds of the invention have formula I:

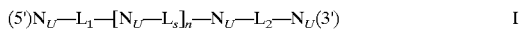

$$(5')N_U-L_1-[N_U-L_s]_n-N_U-L_2-N_U(3') \qquad I$$

wherein:
- each $N_u$ is, independently, a nucleoside that includes a ribose or deoxyribose sugar portion (including 5' and 3' carbon atoms) and a base portion;
- each $L_s$ is a racemic phosphorothioate (i.e., —O—P(S)—O—) internucleoside linkage;
- n is 1–200;
- $L_1$ and $L_2$ are selected such that:
  - $L_1$ is a Sp phosphorothioate internucleoside linkage and $L_2$ is a racemic phosphorothioate internucleoside linkage; or
  - $L_1$ and $L_2$ both are Sp phosphorothioate internucleoside linkages; or
  - $L_1$ is a Rp phosphorothioate internucleoside linkage and $L_2$ is a racemic phosphorothioate internucleoside linkage; or
  - $L_1$ and $L_2$ both are Rp phosphorothioate internucleoside linkages; or
  - $L_1$ and $L_2$, independently, have the formula $CH_2$—O—NR or $CH_2$—NR—O wherein R is H, alkyl having 1 to about 10 carbon atoms, alkenyl having 2 to about 10 carbon atoms, alkynyl having 2 to about 10 carbon atoms; alkaryl having 7 to about 14 carbon atoms, aralkyl having 7 to about 14 carbon atoms.

The present invention also provides methods for modulating the production or activity of a protein in an organism, and methods for treating an organism having a disease characterized by the undesired production of a protein. Such methods involve contacting the organism with one or more of the foregoing compounds.

Also provided are methods for assaying a nucleic acid comprising the step of contacting a solution suspected to contain the nucleic acid with at least one such compound,

DETAILED DESCRIPTION OF THE INVENTION

Figure 1:
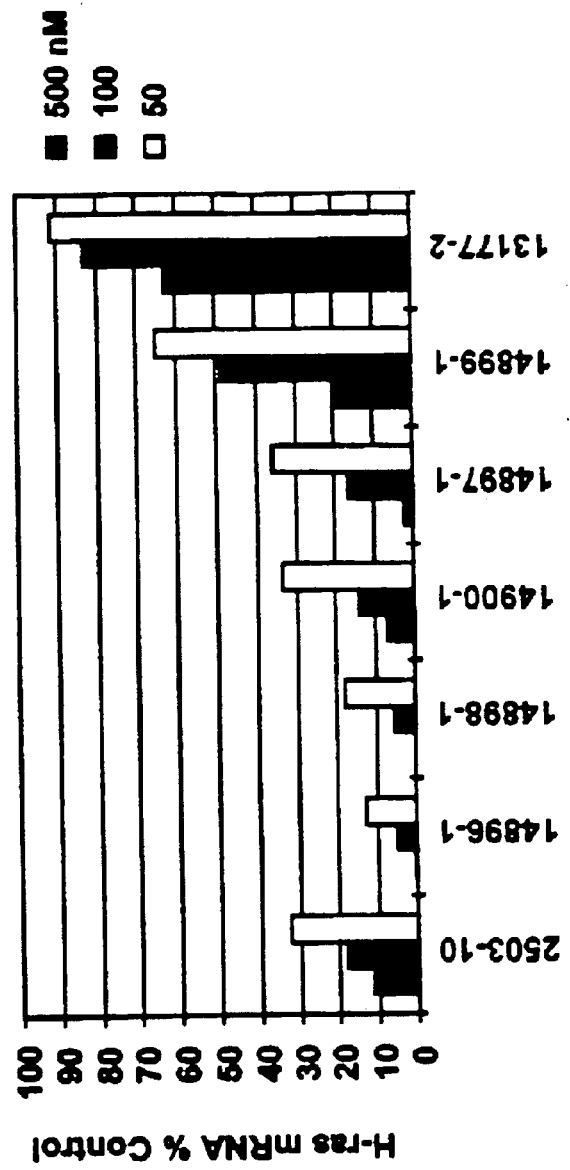
FIGS. 1 and 2 each show a table and a bar graph summarizing properties and inhibition responses for oligonucleotides specifically hybridizable with the activated H-ras gene or scrambled controls (SEQ ID NOs. 6–17 as identified in the Figures). The tables show the nucleobase composition and chemistry at each position along the length of the oligonucleotides. The bar graphs summarize the dose response inhibition of H-ras mRNA in T-24 cells for each of the tested doses of the oligonucleotides.

The term "nucleoside" as used in connection with this invention refers to a unit made up of a heterocyclic base and its sugar. The term "nucleotide" refers to a nucleoside having a phosphate group on its 3' or 5' sugar hydroxyl group.

As used herein, the term "oligonucleotide" is intended to include both naturally occurring and non-naturally occurring (i.e.; "synthetic") oligomers of linked nucleosides. Although such linkages generally are between the 3' carbon of one nucleoside and the 5' carbon of a second nucleoside (i.e., 3'–5' linkages), other linkages (such as 2'–5' linkages) can be formed.

Naturally occurring oligonucleotides are those which occur in nature; for example ribose and deoxyribose phosphodiester oligonucleotides having adenine, guanine, cytosine, thymine and uracil nucleobases. As used herein, non-naturally occurring oligonucleotides are oligonucleotides that contain modified sugar, internucleoside linkage and/or nucleobase moieties. Such oligonucleotide analogs are typically structurally distinguishable from, yet functionally interchangeable with, naturally occurring or synthetic wild type oligonucleotides. Thus, non-naturally occurring oligonucleotides include all such structures which function effectively to mimic the structure and/or function of a desired RNA or DNA strand, for example, by hybridizing to a target.

Representative nucleobases include adenine, guanine, cytosine, uridine, and thymine, as well as other non-naturally occurring and natural nucleobases such as xanthine, hypoxanthine, 2-aminoadenine, 6-methyl and other alkyl derivatives of adenine and guanine, 2-propyl and other alkyl derivatives of adenine and guanine, 5-halo uracil and cytosine, 6-azo uracil, cytosine and thymine, 5-uracil (pseudo uracil), 4-thiouracil, 8-halo, oxa, amino, thiol, thioalkyl, hydroxyl and other 8-substituted adenines and guanines, 5-trifluoromethyl and other 5-substituted uracils and cytosines, 7-methylguanine. Further naturally and non naturally occurring nucleobases include those disclosed in U.S. Pat. No. 3,687,808 (Merigan, et al.), in chapter 15 by Sanghvi, in *Antisense Research and Application*, Ed. S. T. Crooke and B. Lebleu, CRC Press, 1993, in Englisch et al., *Angewandte Chemie*, International Edition, 1991, 30, 613–722 (see especially pages 622 and 623, and in the *Concise Encyclopedia of Polymer Science and Engineering*, J. I. Kroschwitz Ed., John Wiley & Sons, 1990, pages 858–859, Cook, *Anti-Cancer Drug Design* 1991, 6, 585–607, each of which are hereby incorporated by reference in their entirety). The term "nucleosidic base" is further intended to include heterocyclic compounds that can serve as like nucleosidic bases including certain "universal bases" that are not nucleosidic bases in the most classical sense but serve as nucleosidic bases. Especially mentioned as a universal base is 3-nitropyrrole.

Representative 2'-substituents according to the present invention include H, OH, F, and groups of formula

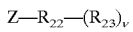

$$Z-R_{22}-(R_{23})_v$$

where:
- Z is O, S, NH, or $N-R_{22}-(R_{23})_v$
- $R_{22}$ is $C_1-C_{20}$ alkyl, $C_2-C_{20}$ alkenyl, or $C_2-C_{20}$ alkynyl;
- $R_{23}$ is hydrogen, amino, halogen, hydroxyl, thiol, keto, carboxyl, nitro, nitroso, nitrile, trifluoromethyl, trifluoromethoxy, O-alkyl, S-alkyl, NH-alkyl, N-dialkyl, O-aryl, S-aryl, NH-aryl, O-aralkyl, S-aralkyl, NH-aralkyl, amino, N-phthalimido, imidazole, azido, hydrazino, hydroxylamino, isocyanato, sulfoxide, sulfone, sulfide, disulfide, silyl, aryl, heterocycle, carbocycle, intercalator, reporter molecule, conjugate, polyamine, polyamide, polyalkylene glycol, polyether, a group that enhances the pharmacodynamic properties of oligonucleotides, or a group that enhances the pharmacokinetic properties of oligonucleotides;
- v is from 0 to about 10.

Additional 2'-substituents have one of the formulas:

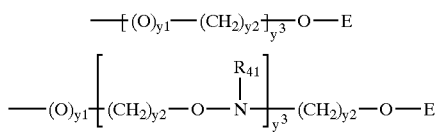

where:
y1 is 0 or 1;
y2 is 0 to 10;
y3 is 1 to 10;
E is $N(R_{41})(R_{42})$ or $N=C(R_{41})(R_{42})$; and
each $R_{41}$ and each $R_{42}$ is independently H, $C_1-C_{10}$ alkyl, a nitrogen protecting group, or $R_{41}$ and $R_{42}$ taken together form a nitrogen protecting group; or $R_{41}$ and $R_{42}$ taken together with the N or C atom to which they are attached form a ring structure that can include at least one heteroatom selected from N and O.

Preferred 2'-groups include H, OH, F, and O-, S-, or N-alkyl groups. One particularly preferred group includes 2'-methoxyethoxy [2'-O—$CH_2CH_2OCH_3$, also known as 2'-O-(2-methoxyethyl) or 2'-MOE] (Martin et al., *Helv. Chim. Acta*, 1995, 78, 486), i.e., an alkoxyalkoxy group. A further preferred modification includes 2'-dimethylaminooxyethoxy, i.e., a $O(CH_2)_2ON(CH_3)_2$ group, also known as 2'-DMAOE, as described in co-owned United States patent application Ser. No. 09/016,520, filed on Jan. 30, 1998, the contents of which are herein incorporated by reference. Other preferred modifications include 2'-methoxy (2'-O—$CH_3$) and 2'-aminopropoxy (2'-$OCH_2CH_2NH_2$).

Sugars having O-substitutions on the ribosyl ring are also amenable to the present invention. Representative substitutions for ring O include S, $CH_2$, CHF, and $CF_2$, see, e.g., Secrist, et al., Abstract 21, *Program & Abstracts, Tenth International Roundtable, Nucleosides, Nucleotides and their Biological Applications*, Park City, Utah, Sep. 16–20, 1992, hereby incorporated by reference in its entirety. Additional modifications may also be made at other positions on the oligonucleotide, particularly the 3' position of the sugar on the 3' terminal nucleotide and the 5' position of 5' terminal nucleotide. For example, one additional modification of the oligonucleotides of the invention involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., *Proc. Natl. Acad. Sci. USA*, 1989, 86, 6553), cholic acid (Manoharan et al., *Bioorg. Med. Chem. Lett.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36, 3651; Shea et al., *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 1996, 277, 923).

As used herein, the term "alkyl" includes but is not limited to straight chain, branch chain, and cyclic unsaturated hydrocarbon groups including but not limited to methyl, ethyl, and isopropyl groups. Alkyl groups of the present invention may be substituted. Representative alkyl substituents are disclosed in U.S. Pat. No. 5,212,295, at column 12, lines 41–50, hereby incorporated by reference in its entirety.

Alkenyl groups according to the invention are to straight chain, branch chain, and cyclic hydrocarbon groups containing at least one carbon—carbon double bond, and alkynyl groups are to straight chain, branch chain, and cyclic hydrocarbon groups containing at least one carbon—carbon triply bond. Alkenyl and alkynyl groups of the present invention can be substituted.

Aryl groups are substituted and unsubstituted aromatic cyclic moieties including but not limited to phenyl, naphthyl, anthracyl, phenanthryl, pyrenyl, and xylyl groups. Alkaryl groups are those in which an aryl moiety links an alkyl moiety to a core structure, and aralkyl groups are those in which an alkyl moiety links an aryl moiety to a core structure.

In general, the term "hetero" denotes an atom other than carbon, preferably but not exclusively N, O, or S. Accordingly, the term "heterocycloalkyl" denotes an alkyl ring system having one or more heteroatoms (i.e., non-carbon atoms). Preferred heterocycloalkyl groups include, for example, morpholino groups. As used herein, the term "heterocycloalkenyl" denotes a ring system having one or more double bonds, and one or more heteroatoms. Preferred heterocycloalkenyl groups include, for example, pyrrolidino groups.

Oligonucleotides according to the present invention that are hybridizable to a target nucleic acid preferably comprise from about 5 to about 50 nucleosides. It is more preferred that such compounds comprise from about 8 to about 30 nucleosides, with 15 to 25 nucleosides being particularly preferred. As used herein, a target nucleic acid is any nucleic acid that can hybridize with a complementary nucleic acid-like compound. Further in the context of this invention, "hybridization" shall mean hydrogen bonding, which may be Watson-Crick, Hoogsteen or reversed Hoogsteen hydrogen bonding between complementary nucleobases. "Complementary" as used herein, refers to the capacity for precise pairing between two nucleobases. For example, adenine and thymine are complementary nucleobases which pair through the formation of hydrogen bonds. "Complementary" and "specifically hybridizable," as used herein, refer to precise pairing or sequence complementarity between a first and a second nucleic acid-like oligomers containing nucleoside subunits. For example, if a nucleobase at a certain position of the first nucleic acid is capable of hydrogen bonding with a nucleobase at the same position of the second nucleic acid, then the first nucleic acid and the second nucleic acid are considered to be complementary to each other at that position. The first and second nucleic acids are complementary to each other when a sufficient number of corresponding positions in each molecule are occupied by nucleobases which can hydrogen bond with each other. Thus, "specifically hybridizable" and "complementary" are terms which are used to indicate a sufficient degree of complementarity such that stable and specific binding occurs between a compound of the invention and a target RNA molecule. It is understood that an oligomeric compound of the invention need not be 100% complementary to its target RNA sequence to be specifically hybridizable. An oligomeric compound is specifically hybridizable when binding of the oligomeric compound to the target RNA molecule interferes with the normal function of the target RNA to cause a loss of utility, and there is a sufficient degree of complementarity to avoid non-specific binding of the oligomeric-compound to non-target sequences under conditions in which specific binding is desired, i.e. under physiological conditions in the case of in vivo assays or therapeutic treatment, or in the case of in vitro assays, under conditions in which the assays are performed.

As will be recognized, modification of the internal phosphorous atom of modified phosphorous-linked oligonucleotides results in Rp and Sp stereoisomers. In accordance with the present invention, a "chirally predominant" (i.e., Rp or Sp) phosphorous-containing linkage is one for which there is at least about a 75% occurrence of one of the stereoisomers (and no more than about a 25% occurrence of the counterpart stereoisomer) among a given collection of isomeric oligonucleotide molecules. Conversely, a "racemic" phosphorous-containing linkage is one for which there is no more than about a 60% occurrence of one of the stereoisomers and at least about a 40% occurrence of the counterpart stereoisomer.

In preferred embodiments, the compound of the invention are present in greater than about 60% stereoisomeric purity (i.e., greater than about 60% purity with respect to counterpart stereoisomers), preferably greater than about 90% stereoisomeric purity, more preferably greater than about 95% stereoisomeric purity.

Phosphorothioate linkages in the oligonucleotides of the invention are prepared using standard phosphoramidite chemistry on, for example, an automated DNA synthesizer (e.g., Applied Biosystems model 380B) and oxidation with 0.2 M solution of 3H-1,2-benzodithiole-3-one 1,1-dioxide in acetonitrile for the stepwise thiation of the phosphite linkages. Phosphorothioate linkages have Sp configuration are prepared generally according to the procedures described in U.S. Pat. Nos. 5,212,295, 5,587,361 and 5,599,797. Linkages of formula $CH_2$—O—NR and $CH_2$—NR—O are prepared generally according to the procedure described in U.S. Pat. No. 5,489,677, which is incorporated herein by reference.

As will be recognized, this invention concerns oligonucleotides that exhibit increased stability relative to their naturally occurring counterparts. Extracellular and intracellular nucleases generally do not recognize (and, therefore, do not bind to) the compounds of the invention. The modified internucleoside linkages of this invention preferably replace naturally-occurring phosphodiester-5'-methylene linkages to confer nuclease resistance.

The oligonucleotides of the invention can be used in diagnostics, therapeutics and as research reagents and kits. They can be used in pharmaceutical compositions by including a suitable pharmaceutically acceptable diluent or carrier. They further can be used for treating organisms having a disease characterized by the undesired production of a protein. The organism should be contacted with an oligonucleotide having a sequence that is capable of specifically hybridizing with a strand of nucleic acid coding for the undesirable protein. Treatments of this type can be practiced on a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, each cell of multicellular eukaryotes can be treated, as they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic oligonucleotides.

Some representative therapeutic indications and other uses for the compounds of the invention are as follows:

One therapeutic indication of particular interest is psoriasis. Psoriasis is a common chronic and recurrent disease characterized by dry, well-circumscribed, silvery, scaling papules and plaques of various sizes. The disease varies in severity from a few lesions to widespread dermatosis with disabling arthritis or exfoliation. The ultimate cause of psoriasis is not known, but the thick scaling that occurs is probably due to increased epidermal cell proliferation (*The Merck Manual of Diagnosis and Therapy*, 15th Ed., pp. 2283–2285, Berkow et al., eds., Rahway, N.J., 1987). Inhibitors of Protein Kinase C (PKC) have been shown to have both antiproliferative and anti-inflammatory effects in vitro. Some antipsoriasis drugs, such as cyclosporin A and anthralin, have been shown to inhibit PKC, and inhibition of PKC has been suggested as a therapeutic approach to the treatment of psoriasis (Hegemann, L. and G. Mahrle, *Pharmacology of the Skin*, H. Mukhtar, ed., pp. 357–368, CRC Press, Boca Raton, Fla., 1992). Antisense compounds targeted to Protein Kinase C (PKC) proteins are described in U.S. Pat. No. 5,620,963 to Cook et al. and U.S. Pat. No. 5,681,747 to Boggs et al.

Another type of therapeutic indication of interest is inflammatory disorders of the skin. These occur in a variety of forms including, for example, lichen planus, toxic epidermal necrolyis (TEN), ertyhema multiforme and the like (*The Merck Manual of Diagnosis and Therapy*, 15th Ed., pp. 2286–2292, Berkow et al., eds., Rahway, N.J., 1987). Expression of ICAM-1 has been associated with a variety of inflammatory skin disorders such as allergic contact dermatitis, fixed drug eruption, lichen planus and psoriasis (Ho et al., *J. Am. Acad. Dermatol.*, 1990, 22, 64; Griffiths et al., *Am. J. Pathology*, 1989, 135, 1045; Lisby et al., *Br. J. Dermatol.*, 1989, 120, 479; Shiohara et al., *Arch. Dermatol.*, 1989, 125, 1371; Regezi et al., *Oral Surg. Oral Med. Oral Pathol.*, 1996, 81, 682). Moreover, intraperitoneal administration of a monoclonal antibody to ICAM-1 decreases ovalbumin-induced eosinophil infiltration into skin in mice (Hakugawa et al., *J. Dermatol.*, 1997, 24, 73). Antisense compounds targeted to ICAM-1 are described in U.S. Pat. Nos. 5,514,788 and 5,591,623, and co-pending U.S. patent application Ser. No. 09/009,490 and Ser. No. 09/062,416, Jan. 20, 1998 and Apr. 17, 1998, respectively, all to Bennett et al.

Other antisense targets for skin inflammatory disorders are VCAM-1 and PECAM-1. Intraperitoneal administration of a monoclonal antibody to VCAM-1 decreases ovalbumin-induced eosinophil infiltration into the skin of mice (Hakugawa et al., *J. Dermatol.*, 1997, 24, 73). Antisense compounds targeted to VCAM-1 are described in U.S. Pat. Nos. 5,514,788 and 5,591,623. PECAM-1 proteins are glycoproteins which are expressed on the surfaces of a variety of cell types (for reviews, see Newman, *J. Clin. Invest.*, 1997, 99, 3 and DeLisser et al., *Immunol. Today,* 1994, 15, 490). In addition to directly participating in cell—cell interactions, PECAM-1 apparently also regulates the activity and/or expression of other molecules involved in cellular interactions (Litwin et al., *J. Cell Biol.,* 1997, 139, 219) and is thus a key mediator of several cell:cell interactions. Antisense compounds targeted to PECAM-1 are described in co-pending U.S. patent application Ser. No. 09/044,506, filed Mar. 19, 1998, by Bennett et al.

Another type of therapeutic indication of interest for oligonucleotides encompasses a variety of cancers of the skin. Representative skin cancers include benign tumors (warts, moles and the like) and malignant tumors such as, for example, basal cell carcinoma, squamous cell carcinoma, malignant melanoma, Paget's disease, Kaposi's sarcoma and the like (*The Merci Manual of Diagnosis and Therapy,* 15th Ed., pp. 2301–2310, Berkow et al., eds., Rahway, N.J., 1987). A number of molecular targets involved in tumorigenesis, maintenance of the hyperproliferative state and metastasis' are targeted to prevent or inhibit skin cancers, or to prevent their spread to other tissues.

The ras oncogenes are guanine-binding proteins that have been implicated in cancer by, e.g., the fact that activated ras oncogenes have been found in about 30% of human tumors generally; this figure approached 100% in carcinomas of the exocrine pancreas (for a review, see Downward, *Trends in Biol. Sci.,* 1990, 15, 469). Antisense compounds targeted to H-ras and K-ras are described in U.S. Pat. No. 5,582,972 to Lima et al., U.S. Pat No. 5,582,986 to Monia et al. and U.S. Pat. No. 5,661,134 to Cook et al., and in published PCT application WO 94/08003.

Protein Kinase C (PKC) proteins have also been implicated in tumorigenesis. Antisense compounds targeted to Protein Kinase C (PKC) proteins are described in U.S. Pat. No. 5,620,963 to Cook et al. and U.S. Pat. No. 5,681,747 to Boggs et al. Also of interest are AP-1 subunits and JNK proteins, particularly in regard to their roles in tumorigenesis and metastasis. The process of metastasis involves a sequence of events wherein (1) a cancer cell detaches from its extracellular matrices, (2) the detached cancer cell migrates to another portion of an animal's body, often via the circulatory system, and (3) attaches to a distal and inappropriate extracellular matrix, thereby created a focus from which a secondary tumor can arise. Normal cells do not possess the ability to invade or metastasize and/or undergo apoptosis (programmed cell death) if such events occur (Ruoslahti, *Sci. Amer.,* 1996, 275, 72). However, many human tumors have elevated levels of activity of one or more matrix metalloproteinases (MMPs) (Stetler-Stevenson et al., *Annu. Rev. Cell Biol.,* 1993, 9, 541; Bernhard et al., *Proc. Natl. Acad. Sci. (U.S.A.),* 1994, 91, 4293. The MMPs are a family of enzymes which have the ability to degrade components of the extracellular matrix (Birkedal-Hansen, *Current Op. Biol.,* 1995, 7, 728). In particular, one member of this family, matrix metalloproteinase-9 (MMP-9), is often found to be expressed only in tumors and other diseased tissues (Himelstein et al., *Invasion & Metastasis,* 1994, 14, 246).

Several studies have shown that regulation of the MMP-9 gene may be controlled by the AP-1 transcription factor (Kerr et al., *Science,* 1988, 242, 1242; Kerr et al., *Cell,* 1990, 61, 267; Gum et al., *J. Biol. Chem.,* 1996, 271, 10672; Hua et al., *Cancer Res.,* 1996, 56, 5279). Inhibition of AP-1 function has been shown to attenuate MMP-9 expression (U.S. patent application Ser. No. 08/837,201). AP-1 is a heterodimeric protein having two subunits, the gene products of fos and jun. Antisense compounds targeted to c-fos and c-jun are described in co-pending U.S. patent application Ser. No. 08/837,201, filed Mar. 14, 1997, by Dean et al.

Furthermore, AP-1 is itself activated in certain circumstances by phosphorylation of the Jun subunit at an amino-terminal position by Jun N-terminal kinases (JNKs). Thus, inhibition of one or more JNKs is expected to result in decreased AP-1 activity and, consequentially, reduced MMP expression. Antisense compounds targeted to JNKs are described in co-pending U.S. patent application Ser. No. 08/910,629, filed Aug. 13, 1997, by Dean et al.

Infectious diseases of the skin are caused by viral, bacterial or fungal agents. In the case of Lyme disease, the tick borne causative agent thereof, the spirochete *Borrelia burgdorferi,* up-regulates the expression of ICAM-1, VCAM-1 and ELAM-1 on endothelial cells in vitro (Boggemeyer et al., *Cell Adhes. Comm.,* 1994, 2, 145). Furthermore, it has been proposed that the mediation of the disease by the anti-inflammatory agent prednisolone is due in part to mediation of this up-regulation of adhesion molecules (Hurtenbach et al., *Int. J. Immunopharmac.,* 1996, 18, 281). Thus, potential targets for therapeutic mediation (or prevention) of Lyme disease include ICAM-1, VCAM-1 and ELAM-1 (supra).

Other infectious disease of the skin which are tractable to treatment using the compositions and methods of the invention include disorders resulting from infection by bacterial, viral or fungal agents (*The Merck Manual of Diagnosis and Therapy,* 15th Ed., pp. 2263–2277, Berkow et al., eds., Rahway, N.J., 1987).

With regards to infections of the skin caused by fungal agents, U.S. Pat. No. 5,691,461 provides antisense compounds for inhibiting the growth of *Candida albicans.*

With regards to infections of the skin caused by viral agents, U.S. Pat. Nos. 5,166,195, 5,523,389 and 5,591,600 provide oligonucleotide inhibitors of Human Immunodeficiency Virus (HIV). U.S. Pat. No. 5,004,810 provides oligomers capable of hybridizing to herpes simplex virus Vmw65 MRNA and inhibiting its replication. U.S. Pat. Nos. 5,194,428 and 5,580,767 provide antisense compounds having antiviral activity against influenzavirus. U.S. Pat. No. 4,806,463 provides antisense compounds and methods using them to inhibit HTLV-III replication. U.S. Pat. Nos. 4,689, 320, 5,442,049, 5,591,720 and 5,607,923 are directed to antisense compounds as antiviral agents specific to cytomegalovirus (CMV). U.S. Pat. No. 5,242,906 provides antisense compounds useful in the treatment of latent Epstein-Barr virus (EBV) infections. U.S. Pat. Nos. 5,248,670, 5,514,577 and 5,658,891 provide antisense compounds useful in the treatment of herpesvirus infections. U.S. Pat. Nos. 5,457,189 and 5,681,944 provide antisense compounds useful in the treatment of papillomavirus infections. The antisense compounds disclosed in these patents, which are herein incorporated by reference, may be used with the compositions of the invention to effect prophylactic, palliative or therapeutic relief from diseases caused or exacerbated by the indicated pathogenic agents.

Antisense oligonucleotides employed in the compositions of the present invention may also be used to determine the nature, function and potential relationship of various genetic components of the body to disease or body states in animals. Heretofore, the function of a gene has been chiefly examined by the construction of loss-of-function mutations in the gene (i.e., "knock-out" mutations) in an animal (e.g., a transgenic mouse). Such tasks are difficult, time-consuming and cannot be accomplished for genes essential to animal development since the "knock-out" mutation would produce a lethal phenotype. Moreover, the loss-of-function phenotype cannot be transiently introduced during a particular part of the animal's life cycle or disease state; the "knock-out" mutation is always present. "Antisense knockouts," that is, the selective modulation of expression of a gene by antisense oligonucleotides, rather than by direct genetic manipulation, overcomes these limitations (see, for example, Albert et al., *Trends in Pharmacological Sciences,* 1994, 15, 250). In addition, some genes produce a variety of mRNA transcripts as a result of processes such as alternative splicing; a "knock-out" mutation typically removes all forms of mRNA transcripts produced from such genes and thus cannot be used to examine the biological role of a particular mRNA transcript. Antisense oligonucleotides have been systemically administered to rats in order to study the role of the N-methyl-D-aspartate receptor in neuronal death, to mice in order to investigate the biological role of protein kinase C-a, and to rats in order to examine the role of the neuropeptide Y1 receptor in anxiety (Wahlestedt et al., *Nature,* 1993, 363:260; Dean et al., *Proc. Natl. Acad. Sci. U.S.A.,* 1994, 91:11762; and Wahlestedt et al., *Science,* 1993, 259:528, respectively). In instances where complex families of related proteins are being investigated, "antisense knockouts" (i.e., inhibition of a gene by systemic administration of antisense oligonucleotides) may represent the most accurate means for examining a specific member of the family (see, generally, Albert et al., *Trends Pharmacol. Sci.,* 1994, 15:250). By providing compositions and methods for the simple non-parenteral delivery of oligonucleotides and other nucleic acids, the present invention overcomes these and other shortcomings.

The administration of therapeutic or pharmaceutical compositions comprising the oligonucleotides of the invention is believed to be within the skill of those in the art. In general, a patient in need of therapy or prophylaxis is administered a composition comprising a compound of the invention, commonly in a pharmaceutically acceptable carrier, in doses ranging from 0.01 ug to 100 g per kg of body weight depending on the age of the patient and the severity of the disorder or disease state being treated. Dosing is dependent on severity and responsiveness of the disease state to be treated, with the course of treatment lasting from several days to several months, or until a cure is effected or a diminution or prevention of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual antisense compounds, and can generally be estimated based on $EC_{50}$s found to be effective in in vitro and in vivo animal models.

In the context of the invention, the term "treatment regimen" is meant to encompass therapeutic, palliative and prophylactic modalities of administration of one or more compositions of the invention. A particular treatment regimen may last for a period of time which will vary depending upon the nature of the particular disease or disorder, its severity and the overall condition of the patient, and may extend from once daily to once every 20 years. Following treatment, the patient is monitored for changes in his/her condition and for alleviation of the symptoms of the disorder or disease state. The dosage of the composition may either be increased in the event the patient does not respond significantly to current dosage levels, or the dose may be decreased if an alleviation of the symptoms of the disorder or disease state is observed, or if the disorder or disease state has been ablated.

An optimal dosing schedule is used to deliver a therapeutically effective amount of the oligonucleotide of the invention. The term "therapeutically effective amount," for the purposes of the invention, refers to the amount of oligonucleotide-containing pharmaceutical composition which is effective to achieve an intended purpose without undesirable side effects (such as toxicity, irritation or allergic response). Although individual needs may vary, determination of optimal ranges for effective amounts of pharmaceutical compositions is within the skill of the art. Human-doses can be extrapolated from animal studies (Katocs et al., Chapter 27 *In: Remington's Pharmaceutical Sciences,* 18th Ed., Gennaro, ed., Mack Publishing Co., Easton, Pa., 1990). Generally, the dosage required to provide an effective amount of a pharmaceutical composition, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect(s) (Nies et al., Chapter 3 *In: Goodman&Gilman's The Pharmacological Basis of Therapeutics,* 9th Ed., Hardman et al., eds., McGraw-Hill, New York, N.Y., 1996).

Following successful treatment, it may be desirable to have the patient undergo maintenance therapy to prevent the recurrence of the disease state, wherein the bioactive agent is administered in maintenance doses, ranging from 0.01 ug to 100 g per kg of body weight, once or more daily, to once every 20 years. For example, in the case of in individual known or suspected of being prone to an autoimmune or inflammatory condition, prophylactic effects may be achieved by administration of preventative doses, ranging from 0.01 ug to 100 g per kg of body weight, once or more daily, to once every 20 years. In like fashion, an individual may be made less susceptible to an inflammatory condition that is expected to occur as a result of some medical treatment, e.g., graft versus host disease resulting from the transplantation of cells, tissue or an organ into the individual.

Prophylactic modalities for high risk individuals are also encompassed by the invention. As used herein, the term "high risk individual" is meant to refer to an individual for whom it has been determined, via, e.g., individual or family history or genetic testing, that there is a significantly higher than normal probability of being susceptible to the onset or recurrence of a disease or disorder. For example, a subject animal could have a personal and/or family medical history that includes frequent occurrences of a particular disease or disorder. As another example, a subject animal could have had such a susceptibility determined by genetic screening according to techniques known in the art (see, e.g., U.S. Congress, Office of Technology Assessment, Chapter 5 *In: Genetic Monitoring and Screening in the Workplace,* OTA-BA-455, U.S. Government Printing Office, Washington, D.C., 1990, pages 75–99). As part of a treatment regimen for a high risk individual, the individual can be prophylactically treated to prevent the onset or recurrence of the disease or disorder. The term "prophylactically effective amount" is meant to refer to an amount of a pharmaceutical composition which produces an effect observed as the prevention of the onset or recurrence of a disease or disorder. Prophylactically effective amounts of a pharmaceutical composition are typically determined by the effect they have compared to the effect observed when a second pharmaceutical composition lacking the active agent is administered to a similarly situated individual.

For therapeutic use the oligonucleotide analog is administered to an animal suffering from a disease modulated by some protein. It is preferred to administer to patients suspected of suffering from such a disease an amount of oligonucleotide analog that is effective to reduce the symptomology of that disease. One skilled in the art can determine optimum dosages and treatment schedules for such treatment regimens.

It is preferred that the RNA or DNA portion which is to be modulated be preselected to comprise that portion of DNA or RNA which codes for the protein whose formation or activity is to be modulated. The targeting portion of the composition to be employed is, thus, selected to be complementary to the preselected portion of DNA or RNA, that is to be an antisense oligonucleotide for that portion.

In accordance with one preferred embodiment of this invention, the compounds of the invention hybridize to HIV mRNA encoding the tat protein, or to the TAR region of HIV mRNA. In another preferred embodiment, the compounds mimic the secondary structure of the TAR region of HIV mRNA, and by doing so bind the tat protein. Other preferred compounds complementary sequences for herpes, papilloma and other viruses.

It is generally preferred to administer the therapeutic agents in accordance with this invention internally such as orally, intravenously, or intramuscularly. Other forms of administration, such as transdermally, topically, or intralesionally may also be useful. Inclusion in suppositories may also be useful. Use of pharmacologically acceptable carriers is also preferred for some embodiments.

This invention is also directed to methods for the selective binding of RNA for research and diagnostic purposes. Such selective, strong binding is accomplished by interacting such RNA or DNA with compositions of the invention which are resistant to degradative nucleases and which hybridize more strongly and with greater fidelity than known oligonucleotides or oligonucleotide analogs.

EXAMPLE 1
Synthesis of MMI-Containing Oligonucleotides
  a. Bis-2'-O-methyl MMI Building Blocks The synthesis of MMI (i.e., R=CH$_3$) dimer building blocks have been described in some preliminary communications (see, e.g., Swayze, et al., *Synlett* 1997, 859; Sanghvi, et al., *Nucleosides & Nucleotides* 1997, 16 907; Swayze, et al., *Nucleosides & Nucleotides* 1997, 16, 971; Dimock, et al., *Nucleosides & Nucleotides* 1997, 16, 1629). Generally, 5'-O-(4,4'-dimethoxytrityl)-2'-O-methyl-3'-C-formyl nucleosides were condensed with 5'-O-(N-methylhydroxylamino)-2'-O-methyl-3'-O-TBDPS nucleosides using 1 equivalent of BH$_3$ pyridine/1 equivalent of pyridinium para-toluene sulfonate (PPTS) in 3:1 MeOH/THF. The resultant MMI dimer blocks were then deprotected at the lower part of the sugar with 15 equivalents of Et$_3$N-2HF in THF. Thus the T*G$^{iBu}$ dimer unit was synthesized and phosphitylated to give T*G(MMI) phosphoramidite. In a similar fashion, A$^{Bz*T}$(MMI) dimer was synthesized, succinylated and attached to controlled pore glass.

b. Oligonucleotide Synthesis

Oligonucleotides were synthesized on a Perseptive Biosystems Expedite 8901 Nucleic Acid Synthesis System. Multiple 1-µmol syntheses were performed for each oligonucleotide. A*$_{MMI}$T solid support was loaded into the column. Trityl groups were removed with trichloroacetic acid (975 µL over one minute) followed by an acetonitrile wash. The oligonucleotide was built using a modified thioate protocol. Standard amidites were delivered (210 µL) over a 3 minute period in this protocol. The T* $_{MMI}$ G amidite was double coupled using 210 µL over a total of 20 minutes. The amount of oxidizer, 3H-1,2-benzodithiole-3-one-1,1-dioxide (Beaucage reagent, 3.4 g Beaucage reagent/200 mL acetonitrile), was 225 µL (one minute wait step). The unreacted nucleoside was capped with a 50:50 mixture of tetrahyrdofuran/acetic anhydride and tetrahydrofuran/pyridine/1-methyl imidazole. Trityl yields were followed by the trityl monitor during the duration of the synthesis. The final DMT group was left intact. After the synthesis, the contents of the synthesis cartridge (1 µmole) was transferred to a Pyrex vial and the oligontcleotide was cleaved from the controlled pore glass (CPG) using 5 mL of 30% ammonium hydroxide (NH$_4$OH) for approximately 16 hours at 55° C.

c. Oligonucleotide Purification

After the deprotection step, the samples were filtered from CPG using Gelman 0.45 µm nylon acrodisc syringe filters. Excess NH$_4$OH was evaporated away in a Savant AS160 automatic SpeedVac. The crude yield was measured on a Hewlett Packard 8452A Diode Array Spectrophotometer at 260 nm. Crude samples were then analyzed by mass spectrometry (MS) on a Hewlett Packard electrospray mass spectrometer. Trityl-on oligonucleotides were purified by reverse phase preparative high performance liquid chromatography (HPLC). HPLC conditions were as follows: Waters 600E with 991 detector; Waters Delta Pak C4 column (7.8×300 mm); Solvent A: 50 mM triethylammonium acetate (TEA-Ac), pH 7.0; B: 100% acetonitrile; 2.5 mL/min flow rate; Gradient: 5% B for first five minutes with linear increase in B to 60% during the next 55 minutes. Fractions containing the desired product (retention time=41 min. for DMT-ON-16314; retention time=42.5 min. for DMT-ON-16315) were collected and the solvent was dried off in the SpeedVac. Oligonucleotides were detritylated in 80% acetic acid for approximately 60 minutes and lyophilized again. Free trityl and excess salt were removed by passing detritylated oligonucleotides through Sephadex G-25 (size exclusion chromatography) and collecting appropriate samples through a Pharmacia fraction collector. The solvent was again evaporated away in a SpeedVac. Purified oligonucleotides were then analyzed for purity by CGE, HPLC (flow rate: 1.5 mL/min; Waters Delta Pak C4 column, 3.9×300 mm), and MS. The final yield was determined by spectrophotometer at 260 nm.

The synthesized oligonucleotides and their physical characteristics are shown, respectively, in Tables I and II. All nucleosides with an asterisk contain MMI linkage.

TABLE I

ICAM-1 Oligonucleotides Containing MMI Dimers Synthesized for in Vivo Nuclease and Pharmacology Studies.

| Oligo # | ISIS # | Sequence (5'-3') | Backbone | 2'-Chemistry |
|---|---|---|---|---|
| 1 | 16314 | TGC ATC CCC CAG GCC ACC A*T (SEQ ID NO.1) | P=S, MMI | Bis-2'--OMe- |
| 2 | 16315 | T*G C ATC CCC CAG GCC ACC (SEQ ID NO.2) | P=S, MMI | MMI, 2'-H Bis-2'- OMe- |
| 3 | 3082 | TGC ATC CCC CAG GCG ACC AT (SEQ ID NO.3) | P=S | 2'-H, single mismatch |

TABLE I-continued

ICAM-1 Oligonucleotides Containing MMI Dimers Synthesized for in Vivo Nuclease and Pharmacology Studies.

| Oligo # | ISIS # | Sequence (5'-3') | Back-bone | 2'-Chem-istry |
|---|---|---|---|---|
| 4 | 13001 | TGC ATC CCC CAG GCC ACC AT (SEQ ID NO.4) | P=S | 2'-H |

TABLE II

Physical Characteristics of MMI Oligomers Synthesized for Pharmacology, and In Vivo Nuclease Studies.

| Sequence (5'-3') | Expected Mass (g) | Observed Mass (g) | HPLC Retn. Time (min.) |
|---|---|---|---|
| 16314 TGC ATC CCC CAG GCC ACC A*T (SEQ ID NO.1) | 6295 | 6297 | 23.9 |
| 16315 T*G C ATG CCC CAG GCC ACC A*T (SEQ ID NO.2) | 6302 | 6303 | 24.75 |

HPLC Conditions: Waters 600E with detector 991; Waters C4 column (3.9 × 300mm); Solvent A: 50 mM TEA-Ac, pH 7.0; B: 100% acetonitrile; 1.5 mL/min. flow rate; Gradient: 5% B for first five minutes with linear increase in B to 60% during the next 55 minutes.

EXAMPLE 2
Synthesis of Sp Terminal Oligonucleotide a. 3'-O-t-Butyldiphenylsilyl-thymidine (1)

5'-O-Dimethoxytritylthymidine is silylated with 1 equivalent of t-butyldiphenylsilyl chloride (TBDPSCl) and 2 equivalents of imidazole in DMF solvent at room temperature. The 5'-protecting group is removed by treating with 3% dichloracetic acid in $CH_2Cl_2$, b. 5'-O-Dimethoxytrityl-thymidin-3'-O-yl-N,N-diisopropylamino (S-pivaloyl-2-mercaptoethoxy) phosphoramidite (2)

5'-O-Dimethoxytrityl thymidine is treated with bis-(N,N-diisopropylamino)-S-pivaloyl-2-mercaptoethoxy phosphoramidite and tetrazole in $CH_2Cl_2/CH_3CN$ as described by Guzaev et al., *Bioorganic & Medicinal Chemistry Letters* 1998, 8, 1123) to yield the title compound.

c. 5'-O-Dimethoxytrityl-2'-deoxy-adenosin-3'-O-yl-N,N-diisopropylamino (S-pivaloyl-2-mercapto ethoxy) phosphoramidite (3)

5'-O-Dimethoxytrityl-N-6-benzoyl-2'-deoxy-adenosine is phosphitylated as in the previous example to yield the desired amidite.

d. 3'-O-t-Butyldiphenylsilyl-2'-deoxy-$N_2$-isobutyryl-guanosine (4)

5'-O-Dimethoxytrityl-2'-deoxy-$N_2$-isobutyryl-guanisine is silylated with TBDPSCl and imidazole in DMF. The 5'-DMT is then removed with 3% DCA in $CH_2Cl_2$.

e. $T_{(Sp)}G$ dimers and $T_{(s)}$ Phosphoramidite

Compounds 4 and 2 are condensed (1:1 equivalents) using 1H-tetrazole in $CH_3CN$ solvent followed by sulfurization employing Beaucage reagent (see, e.g., Iyer, et al., *J. Org. Chem.* 1990, 55, 4693). The dimers (TG) are separated by column chromatography and the silyl group is deprotected using t-butyl ammonium fluoride/THF to give Rp and Sp dimers of $T_SG$. Small amounts of these dimers are completely deprotected and treated with either P1 nuclease or snake venom phosphodiesterase. The R isomer is resistant to P1 nuclease and hydrolyzed by SVPD. The S isomer is resistant to SVPD and hydrolyzed P1 nuclease. The Sp isomer of the fully protected $T_SG$ dimer is phosphitylated to give DMT-T-Sp-G-phosphoramidite.

f. $A_ST$ Dimers and Solid Support Containing $A_{SP}T$ Dimer

Compounds 3 and 1 are condensed using 1H-tetrazole in $CH_3CN$ solvent followed by sulfurization to give AT dimers. The dimers are separated by column chromatography and the silyl group is deprotected with TBAF/THF. The configurational assignments are done generally as in the previous example. The Sp isomer is then attached to controlled pore glass according to standard procedures to give DMT-$A_{SP}$-T-CPG oligomerization with chirally pure Sp dimer units at the termini.

g. Oligonucleotide Synthesis

The oligonucleotide having the sequence T*GC ATC CCC CAG GCC ACC A*T (SEQ ID NO.5) is synthesized, where T*G and A*T represent chiral Sp dimer blocks described above. DMT-$A_{SP}$-T-CPG is taken in the synthesis column and the next 16b residues are built using standard phosphorothioate protocols and 3H-1,2-benzodithiol-3-one 1,1 dioxide as the sulfurizing agent. After building this 18 mer unit followed by final detritylation, the chiral Sp dimer phosphoramidite of 5'-DMT-$T_{SP}$-G amidite is coupled to give the desired antisense oligonucleotide. This compound is then deprotected in 30% $NH_4OH$ over 16 hours and the oligomer purified in HPLC and desalted in Sephader G-25 column. The final oligomer has Sp configuration at the 5'-terminus and 3'-terminus and the interior has diastereomeric mixture of Rp and Sp configurations.

EXAMPLE 3
Evaluation of In Vivo Stability of Oligonucleotides

Mouse Experiment Procedures.

For each oligonucleotide tested, 9 male BALB/c mice (Charles River, Wilmington, Mass.), weighing about 25 g was used (Crooke et al., *J. Pharmacol. Exp. Ther.,* 1996, 277, 923). Following a 1-week acclimation, mice received a single tail vein injection of oligonucleotide (5 mg/kg) administered in phosphate buffered saline (PBS), pH 7.0 One retro-orbital bleed (either 0.25, 0.5, 2 or 4 lv post dose) and a terminal bleed (either 1, 3, 8 or 24 h post dose) were collected from each group. The terminal bleed (approximately 0.6–0.8 ml) was collected by cardiac puncture following ketamine/xylazine anesthesia. The lood was transferred to an EDTA-coated collection tube and entrifuged to obtain plasma. At termination, the liver and kidneys were collected from each mouse. Plasma and tissues homogenates were used for analysis for determination of intact oligonucleotide content by CGE. All samples were immediately frozen on dry ice after collection and stored at −80° C. until analysis.

The capillary gel electrophoretic analysis indicated the relative nuclease resistance of MMI capped oligomers compared to ISIS 3082 (uniform 2'-deoxy phosphorothioate). Because of the resistance of MMI linkage to nucleases, the compound 16314 was found to be stable in plasma while 3082 was not. However, in kidney and liver, the compound 16314 also showed certain amount of degradation. This implied that while 3'-exonuclease is important in plasma, 5'-exonucleases or endonucleases may be active in tissues. To distinguish between these two possibilities, the data from 16315 was analyzed. In plasma as well as in tissues, (liver and kidney) the compound was stable in various time points. (1, 3 and 24 hrs.). The fact that no degradation was detected proved that 5'-exonucleases and 3'-exonuclease are prevalent in tissues and endonucleases are not active. Furthermore, a single linkage (MMI or Sp thioate linkage) is sufficient as a gatekeeper against nucleases.

EXAMPLE 4

Control of ICAM-1 Expression

Cells and Reagents

The bEnd.3 cell line, a brain endothelioma, was the kind gift of Dr. Werner Risau (Max-Planck Institute). Opti-MEM, trypsin-EDTA and DMEM with high glucose were purchased from Gibco-BRL (Grand Island, N.Y.). Dulbecco's PBS was purchased from Irvine Scientific (Irvine, Calif.). Sterile, 12 well tissue culture plates and Facsflow solution were purchased from Becton Dickinson (Mansfield, Mass.). Ultrapure formaldehyde was purchased from Polysciences (Warrington, Pa.). Recombinant human TNF-a was purchased from R&D Systems (Minneapolis, Minn.). Mouse interferon-γ was purchased from Genzyme (Cambridge, Mass.). Fraction V, BSA was purchased from Sigma (St. Louis, Mo.). The mouse ICAM-1-PE, VCAM-1-FITC, hamster IgG-FITC and rat $IgG_{2a}$-PE antibodies were purchased from Pharmingen (San Diego, Calif.). Zeta-Probe nylon blotting membrane was purchased from Bio-Rad (Richmond, Calif.). QuickHyb solution was purchased from Stratagene (La Jolla, Calif.). A cDNA labeling kit, Prime-a-Gene, was purchased from ProMega (Madison, Wis.). NAP-5 columns were purchased from Pharmacia (Uppsala, Sweden).

Oligonucleotide Treatment

Cells were grown to approximately 75% confluency in 12 well plates with DMEM containing 4.5 g/L glucose and 10% FBS. Cells were washed 3 times with Opti-MEM prewarmed to 37° C. Oligonucleotide was premixed with Opti-MEM, serially diluted to desired concentrations and transferred on to washed cells for a 4 hour incubation at 37° C. Media was removed and replaced with normal growth media with or without 5 ng/ml TNF-α and 200 U/ml interferon-γ, incubated for 2 hours for northern blot analysis of mRNA or overnight for flow cytometric analysis of cell surface protein expression.

Flow Cytometry.

After oligonucleotide treatment, cells were detached from the plates with a short treatment of trypsin-EDTA (1–2 min.). Cells were transferred to 12×75 mm polystyrene tubes and washed with 2% BSA, 0.2% sodium azide in D-PBS at 4° C. Cells were centrifuged at 1000 rpm in a Beckman GPR centrifuge and the supernatant was then decanted. ICAM-1, VCAM-1 and the control antibodies were added at 1 ug/ml in 0.3 ml of the above buffer. Antibodies were incubated with the cells for 30 minutes at 4° C. in the dark, under gentle agitation. Cells were washed again as above and then resuspended in 0.3 ml of FacsFlow buffer with 0.5% ultrapure formaldehyde. Cells were analyzed on a Becton Dickinson FACScan. Results are expressed as percentage of control expression, which was calculated as follows: [((CAM expression for oligonucleotide-treated cytokine induced cells)–(basal CAM expression))/((cytokine-induced CAM expression)–(basal CAM expression))]×100. For the experiments involving cationic lipids, both basal and cytokine-treated control cells were pretreated with Lipofectin for 4 hours in the absence of oligonucleotides.

The results reveal the following: 1) Isis 3082 showed an expected dose response (25–200 nM); 2) Isis 13001 lost its ability to inhibit ICAM-1 expression as expected from a mismatch compound, thus proving an antisense mechanism; 3) 3'-MMI capped oligomer 16314 improved the activity of 3082, and at 200 nM concentration, nearly twice as active as 3082; 4) 5'- and 3'- MMI capped oligomer is the most potent compound and it is nearly 4 to 5 times more efficacious than the parent compound at 100 and 200 nM concentrations. Thus, improved nuclease resistance increased the potency of the antisense oligonucleotides.

EXAMPLE 5

Control of H-ras Expression

Figure 2:

Oligonucleotides having the structures shown in FIGS. 1 and 2 were tested for their ability to inhibit production of H-ras mRNA in T-24 cells. For these test, T-24 cells were plated in 6-well plates and then treated with various escalating concentrations of oligonucleotide in the presence of cationic lipid (Lipofectin, GIBCO) at the ratio of 2.5 μg/ml Lipofectin per 100 nM oligonucleotide. Oligonucleotide treatment was carried out in serum free media for 4 hours. Eighteen hours after treatment the total RNA was harvested and analyzed by northern blot for H-ras mRNA and control gene G3PDH. The data is presented in FIGS. 1 and 2 in bar graphs as percent control normalized for the G3PDH signal. As can be seen, the oligonucleotide having a single MMI linkage in each of the flank regions showed significant reduction of H-ras mRNA.

EXAMPLE 6

5-Lipoxygenase Analysis and Assays

A. Therapeutics

For therapeutic use, an animal suspected of having a disease characterized by excessive or abnormal supply of 5-lipoxygenase is treated by administering the macromolecule of the invention. Persons of ordinary skill can easily determine optimum dosages, dosing methodologies and repetition rates. Such treatment is generally continued until either a cure is effected or a diminution in the diseased state is achieved. Long term treatment is likely for some diseases.

B. Research Reagents

The oligonucleotides of this invention will also be useful as research reagents when used to cleave or otherwise modulate 5-lipoxygenase mRNA in crude cell lysates or in partially purified or wholly purified RNA preparations. This application of the invention is accomplished, for example, by lysing cells by standard methods, optimally extracting the RNA and then treating it with a composition at concentrations ranging, for instance, from about 100 to about 500 ng per 10 Mg of total RNA in a buffer consisting, for example, of 50 mm phosphate, pH ranging from about 4–10 at a temperature from about 30° to about 50° C. The cleaved 5-lipoxygenase RNA can be analyzed by agarose gel electrophoresis and hybridization with radiolabeled DNA probes or by other standard methods.

C. Diagnostics

The oligonucleotides of the invention will also be useful in diagnostic applications, particularly for the determination of the expression of specific mRNA species in various tissues or the expression of abnormal or mutant RNA species. In this example, while the macromolecules target a abnormal mRNA by being designed complementary to the abnormal sequence, they would not hybridize to normal mRNA.

Tissue samples can be homogenized, and RNA extracted by standard methods. The crude homogenate or extract can be treated for example to effect cleavage of the target RNA. The product can then be hybridized to a solid support which contains a bound oligonucleotide complementary to a region on the 5' side of the cleavage site. Both the normal and abnormal 5' region of the mRNA would bind to the solid support. The 3' region of the abnormal RNA, which is cleaved, would not be bound to the support and therefore would be separated from the normal mRNA.

Targeted mRNA species for modulation relates to 5-lipoxygenase; however, persons of ordinary skill in the art will appreciate that the present invention is not so limited and it is generally applicable. The inhibition or modulation of production of the enzyme 5-lipoxygenase is expected to have significant therapeutic benefits in the treatment of disease. In order to assess the effectiveness of the compositions, an assay or series of assays is required.

D. In Vitro Assays

The cellular assays for 5-lipoxygenase preferably use the human promyelocytic leukemia cell line HL-60. These cells can be induced to differentiate into either a monocyte like cell or neutrophil like cell by various known agents. Treatment of the cells with 1.3% dimethyl sulfoxide, DMSO, is known to promote differentiation of the cells into neutrophils. It has now been found that basal HL-60 cells do not synthesize detectable levels of 5-lipoxygenase protein or secrete leukotrienes (a downstream product of 5-lipoxygenase). Differentiation of the cells with DMSO causes an appearance of 5-lipoxygenase protein and leukotriene biosynthesis 48 hours after addition of DMSO. Thus induction of 5-lipoxygenase protein synthesis can be utilized as a test system for analysis of oligonucleotides which interfere with 5-lipoxygenase synthesis in these cells.

A second test system for oligonucleotides makes use of the fact that 5-lipoxygenase is a "suicide" enzyme in that it inactivates itself upon reacting with substrate. Treatment of differentiated HL-60 or other cells expressing 5 lipoxygenase, with 10 $\mu$M A23187, a calcium ionophore, promotes translocation of 5-lipoxygenase from the cytosol to the membrane with subsequent activation of the enzyme. Following activation and several rounds of catalysis, the enzyme becomes catalytically inactive. Thus, treatment of the cells with calcium ionophore inactivates endogenous 5-lipoxygenase. It takes the cells approximately 24 hours to recover from A23187 treatment as measured by their ability to synthesize leukotriene $B_4$. Macromolecules directed against 5-lipoxygenase can be tested for activity in two HL-60 model systems using the following quantitative assays. The assays are described from the most direct measurement of inhibition of 5-lipoxygenase protein synthesis in intact cells to more downstream events such as measurement of 5-lipoxygenase activity in intact cells.

A direct effect which oligonucleotides can exert on intact cells and which can be easily be quantitated is specific inhibition of 5-lipoxygenase protein synthesis. To perform this technique, cells can be labeled with $^{35}$S-methionine (50 $\mu$Ci/mL) for 2 hours at 37° C. to label newly synthesized protein. Cells are extracted to solubilize total cellular proteins and 5-lipoxygenase is immunoprecipitated with 5-lipoxygenase antibody followed by elution from protein A Sepharose beads. The immunoprecipitated proteins are resolved by SDS-polyacrylamide gel electrophoresis and exposed for autoradiography. The amount of immunoprecipitated 5-lipoxygenase is quantitated by scanning densitometry.

A predicted result from these experiments would be as follows. The amount of 5-lipoxygenase protein immunoprecipitated from control cells would be normalized to 100%. Treatment of the cells with 1 $\mu$M, 10 $\mu$M, and 30 $\mu$M of the macromolecules of the invention for 48 hours would reduce immunoprecipitated 5-lipoxygenase by 5%, 25% and 75% of control, respectively.

Measurement of 5-lipoxygenase enzyme activity in cellular homogenates could also be used to quantitate the amount of enzyme present which is capable of synthesizing leukotrienes. A radiometric assay has now been developed for quantitating 5-lipoxygenase enzyme activity in cell homogenates using reverse phase HPLC. Cells are broken by sonication in a buffer containing protease inhibitors and EDTA. The cell homogenate is centrifuged at 10,000×g for 30 min and the supernatants analyzed for 5-lipoxygenase activity. Cytosolic proteins are incubated with 10 $\mu$M $^{14}$C-arachidonic acid, 2 mM ATP, 50 $\mu$M free calcium, 100 $\mu$g/ml phosphatidylcholine, and 50 mM bis-Tris buffer, pH 7.0, for 5 min at 37° C. The reactions are quenched by the addition of an equal volume of acetone and the fatty acids extracted with ethyl acetate. The substrate and reaction products are separated by reverse phase HPLC on a Novapak C18 column (Waters Inc., Millford, Mass.). Radioactive peaks are detected by a Beckman model 171 radiochromatography detector. The amount of arachidonic acid converted into di-HETE's and mono-HETE's is used as a measure of 5-lipoxygenase activity.

A predicted result for treatment of DMSO differentiated HL-60 cells for 72 hours with effective the macromolecules of the invention at 1 $\mu$M, 10 $\mu$M, and 30 $\mu$M would be as follows. Control cells oxidize 200 pmol arachidonic acid/5 min/$10^6$ cells. Cells treated with 1 $\mu$M, 10 $\mu$M, and 30 $\mu$M of an effective oligonucleotide would oxidize 195 pmol, 140 pmol, and 60 pmol of arachidonic acid/5 min/$10^6$ cells respectively.

A quantitative competitive enzyme linked immunosorbant assay (ELISA) for the measurement of total 5-lipoxygenase protein in cells has been developed. Human 5-lipoxygenase expressed in *E. coli* and purified by extraction, Q-Sepharose, hydroxyapatite, and reverse phase HPLC is used as a standard and as the primary antigen to coat microtiter plates. 25 ng of purified 5-lipoxygenase is bound to the microtiter plates overnight at 4° C. The wells are blocked for 90 min with 5% goat serum diluted in 20 mM Tris●HCL buffer, pH 7.4, in the presence of 150 mM NaCl (TBS). Cell extracts (0.2% Triton X-100, 12,000×g for 30 min.) or purified 5-lipoxygenase were incubated with a 1:4000 dilution of 5-lipoxygenase polyclonal antibody in a total volume of 100 $\mu$L in the microtiter wells for 90 min. The antibodies are prepared by immunizing rabbits with purified human recombinant 5-lipoxygenase. The wells are washed with TBS containing 0.05% tween 20 (TBST), then incubated with 100 $\mu$L of a 1:1000 dilution of peroxidase conjugated goat anti-rabbit IgG (Cappel Laboratories, Malvern, Pa.) for 60 min at 25° C. The wells are washed with TBST and the amount of peroxidase labeled second antibody determined by development with tetramethylbenzidine.

Predicted results from such an assay using a 30 mer oligonucleotide at 1 $\mu$M, 10 $\mu$M, and 30 $\mu$M would be 30 ng, 18 ng and 5 ng of 5-lipoxygenase per 106 cells, respectively with untreated cells containing about 34 ng 5-lipoxygenase.

A net effect of inhibition of 5-lipoxygenase biosynthesis is a diminution in the quantities of leukotrienes released from stimulated cells. DMSO-differentiated HL-60 cells release leukotriene B4 upon stimulation with the calcium ionophore A23187. Leukotriene B4 released into the cell medium can be quantitated by radioimmunoassay using commercially available diagnostic kits (New England Nuclear, Boston, Mass.). Leukotriene B4 production can be detected in HL-60 cells 48 hours following addition of DMSO to differentiate the cells into a neutrophil-like cell. Cells ($2\times10^5$ cells/mL) will be treated with increasing concentrations of the macromolecule for 48–72 hours in the presence of 1.3% DMSO. The cells are washed and resuspended at a concentration of $2\times10^6$ cell/mL in Dulbecco's phosphate buffered saline containing 1% delipidated bovine serum albumin. Cells are stimulated with 10 $\mu$M calcium ionophore A23187 for 15 min and the quantity of LTB4 produced from $5\times10^5$ cell determined by radioimmunoassay as described by the manufacturer.

Using this assay the following results would likely be obtained with an oligonucleotide directed to the 5-LO mRNA. Cells will be treated for 72 hours with either 1 $\mu$M, 10 $\mu$M or 30 $\mu$M of the macromolecule in the presence of 1.3% DMSO. The quantity of $LTB_4$ produced from $5\times10^5$ cells would be expected to be about 75 pg, 50 pg, and 35 pg, respectively with untreated differentiated cells producing 75 pg $LTB_4$.

E. In Vivo Assay

Inhibition of the production of 5-lipoxygenase in the mouse can be demonstrated in accordance with the following protocol. Topical application of arachidonic acid results in the rapid production of leukotriene $B_4$, leukotriene $C_4$ and prostaglandin $E_2$ in the skin followed by edema and cellular infiltration. Certain inhibitors of 5-lipoxygenase have been known to exhibit activity in this assay. For the assay, 2 mg of arachidonic acid is applied to a mouse ear with the contralateral ear serving as a control. The polymorphonuclear cell infiltrate is assayed by myeloperoxidase activity in homogenates taken from a biopsy 1 hour following the administration of arachidonic acid. The edematous response is quantitated by measurement of ear thickness and wet weight of a punch biopsy. Measurement of leukotriene $B_4$ produced in biopsy specimens is performed as a direct measurement of 5-lipoxygenase activity in the tissue. Oligonucleotides will be applied topically to both ears 12 to 24 hours prior to administration of arachidonic acid to allow optimal activity of the compounds. Both ears are pretreated for 24 hours with either 0.1 µmol, 0.3 µmol, or 1.0 µmol of the macromolecule prior to challenge with arachidonic acid. Values are expressed as the mean for three animals per concentration. Inhibition of polymorphonuclear cell infiltration for 0.1 µmol, 0.3 µmol, and 1 µmol is expected to be about 10%, 75% and 92% of control activity, respectively. Inhibition of edema is expected to be about 3%, 58% and 90%, respectively while inhibition of leukotriene $B_4$ production would be expected to be about 15%, 79% and 99%, respectively.

Those skilled in the art will appreciate that numerous changes and modifications can be made to the preferred embodiments of the invention and that such changes and modifications can be made without departing from the spirit of the invention. It is therefore intended that the appended claims cover all such equivalent variations as fall within the true spirit and scope of the invention.

What is claimed is:

1. A method of assaying a nucleic acid, comprising:

(a) contacting a solution suspected to contain said nucleic acid with a compound comprising a plurality of covalently-bound nucleosides, the compound being capable of binding to said nucleic acid; said compound having the formula:

$$(5')N_U\text{—}L_1\text{—}[N_U\text{—}L_S]_n\text{—}N_U\text{—}L_2\text{—}N_U(3')$$

wherein:

each $N_U$ is, independently, a nucleoside that includes a ribose or deoxyribose sugar portion and a base portion;

$L_S$ is a racemic phosphorothioate internucleoside linkage;

n is 1–200; and $L_1$ and $L_2$ are independently selected such that:

$L_1$ is a Sp phosphorothioate internucleoside linkage, $L_2$ is a racemic phosphorothioate internucleoside linkage, and said compound has greater than about 60% stereoisomeric purity; or $L_1$ and $L_2$ both are Sp phosphorothioate internucleoside linkages and said compound has greater than about 60% stereoisomeric purity; or $L_1$ is a Rp phosphorothioate internucleoside linkage, $L_2$ is a racemic phosphorothioate internucleoside linkage, and said compound has greater than about 60% stereoisomeric purity; or $L_1$ and $L_2$ both are Rp phosphorothioate internucleoside linkages and said compound has greater than about 60% stereoisomeric purity; or $L_1$ and $L_2$, independently, have the formula $CH_2$—O—NR or $CH_2$—NR—O wherein R is H, alkyl having 1 to about 10 carbon atoms, alkenyl having 2 to about 10 carbon atoms, alkynyl having 2 to about 10 carbon atoms; alkaryl having 7 to about 14 carbon atoms, aralkyl having 7 to about 14 carbon atoms; and (b) determining if said nucleic acid is present by determining if said binding has occurred.

2. The method of claim 1 wherein $L_1$ is a Sp phosphorothioate internucleoside linkage and $L_2$ is a racemic phosphorothioate internucleoside linkage.

3. The method of claim 1 wherein $L_1$ and $L_2$ both are Sp phosphorothioate internucleoside linkages.

4. The method of claim 1 wherein $L_1$ is a Rp phosphorothioate internucleoside linkage and $L_2$ is a racemic phosphorothioate internucleoside linkage.

5. The method of claim 1 wherein $L_1$ and $L_2$ both are Rp phosphorothioate internucleoside linkages.

6. The method of claim 1 wherein $L_1$ or $L_2$ is $CH_2$—O—NR.

7. The method of claim 1 wherein $L_1$ or $L_2$ is $CH_2$—NR—O.

8. The method of claim 1 wherein $L_1$ and $L_2$ are both $CH_2$—O—NR.

9. The method of claim 1 wherein $L_1$ and $L_2$ are both $CH_2$—NR—O.

10. The method of claim 1 wherein R is alkyl.

11. The method of claim 1 wherein R is methyl.

12. The method of claim 1 wherein at least one of said nucleosides includes a ribose sugar portion.

13. The method of claim 1 wherein at least one of said nucleosides includes a deoxyribose sugar portion.

14. The method of claim 1 wherein n is about 5 to about 50.

15. The method of claim 1 wherein n is about 8 to about 30.

* * * * *

UNITED STATES PATENT AND TRADEMARK OFFICE
CERTIFICATE OF CORRECTION

PATENT NO. : 6,811,975 B2  Page 1 of 1
DATED : November 2, 2004
INVENTOR(S) : Phillip Dan Cook et al.

It is certified that error appears in the above-identified patent and that said Letters Patent is hereby corrected as shown below:

<u>Title page,</u>
Item [56], References Cited, OTHER PUBLICATIONS,
"Stanley-Crooke" reference, delete "Stanley-Crooke" and insert -- Stanley Crooke --;

<u>Column 29,</u>
Line 6, delete "binding" and insert -- specifically hybridizing --;

<u>Column 30,</u>
Line 5, delete "binding" and insert -- hybridization --.

Signed and Sealed this

Thirtieth Day of May, 2006

JON W. DUDAS
*Director of the United States Patent and Trademark Office*